United States Patent
Uvnäs-Moberg et al.

(10) Patent No.: US 6,262,021 B1
(45) Date of Patent: Jul. 17, 2001

(54) USE OF SUBSTANCES HAVING OXYTOCIN ACTIVITY FOR PREPARATION OF MEDICAMENTS FOR WOUND HEALING

(75) Inventors: Kerstin Uvnäs-Moberg, Djursholm; Thomas Lundeberg, Lidingö, both of (SE)

(73) Assignee: EntreTech Medical AB, Malmo (SE)

( * ) Notice: Subject to any disclaimer, the term of this patent is extended or adjusted under 35 U.S.C. 154(b) by 0 days.

(21) Appl. No.: 09/381,799

(22) PCT Filed: Mar. 26, 1998

(86) PCT No.: PCT/SE98/00554

§ 371 Date: Sep. 24, 1999

§ 102(e) Date: Sep. 24, 1999

(87) PCT Pub. No.: WO98/43661

PCT Pub. Date: Oct. 8, 1998

(30) Foreign Application Priority Data

Mar. 27, 1997 (SE) .................................... 9701162

(51) Int. Cl.$^7$ .............................. A61K 38/11; C07K 7/16
(52) U.S. Cl. ................. 514/11; 514/15; 530/315
(58) Field of Search .............................. 530/315; 514/11, 514/15

(56) References Cited

U.S. PATENT DOCUMENTS 3,274,060 * 9/1966 Bossinger .............................. 514/11
3,352,843 * 11/1967 Boissonnas et al. .................. 530/315
5,175,144 * 12/1992 Walser ...................................... 514/2

FOREIGN PATENT DOCUMENTS

WO 88/05661   8/1988 (WO).

OTHER PUBLICATIONS

Argidas et al. Penile Erection and Yawning Induced by Oxytocin . . . Peptides. vol. 10, pp. 559–563, 1989.*

Shemin et al. Oral Estrogens Decrease Bleeding Time . . . Am. J. Med. vol. 89, pp. 436–440, Oct. 1990.*

Review of Surgery, vol. 32, No. 6, 1975, "A Review of Recent Therapeutic Approaches to Treatment of Stress Ulcers," Romero et al.; pp. 379–388.

Annals of Plastic Surgery, vol. 31, No. 1, 1993, "Control of Hemorrhage During Renal Failure with Triglycyl–L–ysine–Vasopressin," Garner et al., pp. 78–81.

* cited by examiner

Primary Examiner—Jeffrey E. Russel
(74) Attorney, Agent, or Firm—Nixon & Vanderhye P.C.

(57) ABSTRACT

Substances having oxytocin activity can be used for the preparation of a pharmaceutical composition for the curative or prophylactic treatment of wounds, such as chronic wounds. The wound healing effect can be strengthened or prolonged by combining oxytocin with estrogen.

22 Claims, 1 Drawing Sheet

FIGURE 1

USE OF SUBSTANCES HAVING OXYTOCIN ACTIVITY FOR PREPARATION OF MEDICAMENTS FOR WOUND HEALING

The present invention refers to a new use of oxytocin.

BACKGROUND OF THE INVENTION

A lesion or wound can be obtained either by external damage, giving a traumatic wound emanating from an accident or a surgical operation, or by a pathological process in the tissue. An ulcer, such as peptic and bone ulcer, mainly refers to a wound in the skin or membranes. Lesions also comprises damages in varying other tissues, such as bone fractures. In this description the expression wound is used for all types of damages of the human or animal body. Wounds can be classified as an acute or a chronic wound.

The mechanisms involved in wound healing can generally be divided into four phases, that is hemostasis, inflammation, proliferation and maturation. During the inflammation leucocytes are accumulated in order to combat bacteria and the permeability of the walls of the vessels is increased leading to swelling. Many of said substances also promotes an improved microcirculation leading to redness and heat. If an infection is not developed the number of leucocytes will be reduced and replaced by monocytes that is macrophages and lymphocytes releasing i.e. growth factors (cytokines) as well as a number of chemical substances, such as histamine, serotonin, prostaglandins, which are the main regulators of the beginning as well as the continuation of the wound healing process. The most important regulating cell is the macrophage. In the proliferation phase connective tissue is formed, new blood vessels are growing in and injured tissue is regenerated. Fibroblasts are the dominating cells after about a week, the inflammation decreases and the strength of the wound is rapidly increased. During the maturation phase, finally, the tissue protein collagen is stabilised and scar tissue is formed. This phase might go on for a long time during which the strength is improved and the regeneration is continued, for instance of nerve tissue. In order to obtain an optimal wound healing the supply of different vitamins and trace elements as well as nutrients should be sufficient as well as the oxygen supply.

Uncompromised cellular homeostasis is essential for wound healing and repair and in the healing tissue certain conditions are required for the development of granulation tissue and epithelial budding. The homeostatic conditions include the degree of hydration, sufficient blood perfusion, availability of various growth factors, an appropriate partial pressure of oxygen, acceptable levels of nonpathogenic microflora and maintenance of voltage gradients between the wound and adjacent normal skin. In a homeostatic environment cells are bathed in body fluids that allow for normal growth and repair processes.

Chronic wounds or indolent, nonhealing wounds may arise from different causes including infection, the presence of foreign bodies or toxic irritants, burns, prolonged cutaneously applied pressure and poor blood supply owing to impaired circulation. In a chronic wound the tissue homeostasis and the wound environment are compromised so that either healing fails to occur or healing begins but is subsequently halted. Factors involved in said conditions are tissue necrosis, dehydration, chronic wound edema, fibrotic induration and small blood vessel disease.

Leg ulcer is one type of chronic wounds which is found in a substantial part of the population, increasing with advancing age. The course of the disease can last from a couple of months up to several decades and will bring about heavy expenses for the society as well as a great suffering for the individual patient. Pressure ulcer, decubitus ulcer, or bedsore is another type of chronic wounds which mainly affects elderly people. Chronic non-healing ulcers are a serious problem in diabetic patients.

In order to provide a homeostatic environment the wound can be covered with an occlusive dressing designed to keep the wound moist. This will however bring about a risk of promoting wound infection.

One of the oldest therapeutic methods used for treating chronic open wounds is hydrotherapy, which today can be performed in a whirlpool bath. By this adherent dressings can be soaked off and necrotic tissue debrided.

In chronic dermal and indolent ulcers cell migration from the wound periphery may not occur if necrotic, desiccated tissue is obstructing it. The necrotic tissue impedes the formation of granulation tissue and prevents epithelial cells from migrating across the wound. Debridement, that is the removal of necrotic tissue from a wound, is therefore necessary not only to remove dead tissue on which bacteria survive to allow the healing processes of granulation development and fibroblastic deposition of collagen upon which the epidermal cells can migrate and close the wound, but also to remove many of the microorganisms that may be present. This debridement can be performed by topical application of enzymes, by facilitating autolysis, that is self-digestion of necrotic tissue by enzymes that are naturally present in wound fluids, with synthetic dressings or by surgical excision. Once debrided a wound will normally undergo granulation, contraction and epithelialization.

There are a number of topical agents which can have a profound effect on the rate of wound healing. Topical antimicrobials and cleansers have frequently been overused in wound therapy resulting in harmful cytotoxic effects and minimal antimicrobial and cleansing effectiveness. As examples of such agents can be mentioned iodophor, sodium hypochlorite solution, hydrogen peroxide and zinc oxide.

It has been hypothesized that impaired wound healing may result from lack of adequate stimulation by growth factors.

In fact growth factors have been used in clinical trials to test if they can improve wound closure in patients with chronic nonhealing wounds. Recently promising animal experiments on wound healing have been performed with growth factors, but a local administration on chronic wounds in humans has not been as successful. It has been suggested to use several different growth factors in combination with a protease inhibitor.

Another approach has been to transplant epithelial cells alone or in combination with fibroblasts and extracellular matrix components. It has also been speculated in the use of genes regulating the synthesis of healing polypeptides in the transplanted cells or applied directly on the wound.

PRIOR ART

Growth factors that are mitogenic or chemotactic or that promote the differentiation of one or more types of cells that participate in the repair of injured skin could, in principle, promote cutaneous healing. The fibroblast growth factors (FGFs) are a family of nine known homologous mitogens that stimulate cells of mesodermal and ectodermal origin through at least four unique membrane-spanning tyrosine kinase receptors and their alternatively transcribed variants. Acidic FGF (aFGF or FGF-1) appears to be unique among the characterized FGFs in its ability to bind all known FGF receptors with high affinity. This broad receptor specificity presumably contributes to its multiple cellular targets in vitro and diverse therapeutically relevant biologic activities in animal models of tissue repair. aFGF is a short polypeptide that is a potent mitogen for dermal fibroblasts, vascular endothelial cells, and epidermal keratinocytes, the principal cells in skin. In addition, aFGF is chemotactic for vascular endothelial cells in vitro and induces new blood vessel growth in vivo. In rats and mice, exogenously applied aFGF promotes healing of full-thickness dermal wounds and produces a transient increase of tensile strength in incisional wounds. Liying Sun et al., Transfection with aFGF cDNA improves wound healing, The Journal of Investigative Dermatology, Vol. 108, No. 3, 1997. Applications of aFGF have been limited, however, because of the necessity to administer relatively large amounts of recombinant aFGF that is often blocked from reaching the target tissue by eschar. The short half-life of aFGF is another drawback of topical application that necessitates frequent doing. Frequent application of aFGF with high doses to overcome diffusion problems can be costly.

Another family of growth factors is transforming growth factor β, TGF-β, comprising a broad variety of polypeptides with multiple biologic activities. The important role of TGF-β1, -β2 and -β3 in wound repair has been demonstrated. TGF-β1 is an important modulator of skin morphogenesis and cutaneous wound repair, and exogenous application to a wound has been shown to enhance the wound healing process in animals. In order to gain insight into the mechanisms of TGF-β1 action genes regulated by this factor in cultured keratinocytes have been identified and cloned, see B. Munz et al., Differential Expression of the Calpactin I Subunits Annexin II and p11 in Cultured Keratinocytes and During Wound Repair, The Journal of Investigative Dermatology, Vol. 108, No. 3, 1997. In addition said substances were also increased by epidermal growth factor, EGF, and keratinocyte growth factor, KGF, which both are stimulating the keratinocyte proliferation.

P. Luppi et al., NGF is released into plasma during human pregnancy; an oxytocin-mediated response?, Neuroreport, 4(8), 1063–5, 1993, has demonstrated a five-fold increase of biologically active nerve growth factor, NGF, in the peripheral circulation of women during pregnancy, labour and lactation. As intravenous injection of oxytocin in female rats has also produced an increase in the hypothalamic levels of NGF it is speculated that the increased amounts of circulating NGF might be correlated with either the high levels of oxytocin in plasma or the activation of the hypothalamo-pituitary-adrenal axis.

G. Jansen et al., Increased survival of ischaemic musculocutaneous flaps in rats after acupuncture, Acta Physiol. Scand., 135, 555–558, 1989, investigated the effects of acupuncture on the survival of flaps in rats and showed that manual acupuncture and electro-acupuncture significantly increased the survival of said flaps compared to untreated controls.

DESCRIPTION OF THE INVENTION

It has now surprisingly been found that oxytocin has a wound healing effect. This healing effect can at least in part be ascribed to the fact that oxytocin activates growth factors of importance for the healing of different tissues. In particular it has now been found that growth factors of the FGF type and/or their receptors are activated by the administration of oxytocin.

The invention refers to the use of a substance with oxytocin activity for the preparation of a pharmaceutical composition for the curative or prophylactic treatment of wounds in mammals including man.

A preferred use is for the treatment of wounds in skin, bone, mucus, tendons, muscles, nerves, vessels and connective tissue.

Another preferred use of the invention is for the treatment of chronic wounds.

Oxytocin was one of the first peptide hormones to be isolated and sequenced. It is a nonapeptide with two cysteine residues that form a disulfide bridge between positions 1 and 6 and corresponds to the formula (SEQ ID No: 9)

For a long time the only effects attributed to oxytocin were its stimulating effects on milk ejection and uterine contractions, but in the past decades it has been shown that oxytocin exerts a wide spectrum of effects within the CNS. It has been suggested that oxytocin participates in the control of memory and learning processes and of various types of behaviour such as feeding, locomotion, as well as maternal and sexual behaviour. Oxytocin is also suggested to participate in the control of cardiovascular functions, thermoregulation, pain threshold and fluid balance. There is also evidence that oxytocin is involved in the control of various immunological processes. It has recently been demonstrated that oxytocin injections cause a lowering of blood pressure and increased weight gain—long lasting effects after repetitive administration.

There are different processes described for the synthetical production of oxytocin; commercial processes are for instance described in U.S. Pat. Nos.2,938,891 and 3,076,797.

In the human body oxytocin is produced in the paraventricular nucleus, PVN, and the supraoptic nucleus, SON, of the hypothalamus. It differs by only two amino acids from vasopressin, which is also produced in these nuclei. The magnocellular oxytocinergic neurons of the SON and PVN send projections into the posterior pituitary gland from which oxytocin or vasopressin are secreted into the circulation. Parvocellular neurons that originate in the PVN project into multiple areas within the central nervous system, CNS. The oxytocin-producing cells are innervated by cholinergic, catecholaminergic as well as peptidergic neurons. The presence of oxytocin in different tissues outside the brain, such as the uterus, ovaries, testis, thymus, adrenal medulla and pancreas has been demonstrated and oxytocin is suggested to exert local effects in these organs.

A parallel secretion of oxytocin into the brain regions and into the circulation occurs in response to some stimuli such as suckling, but other stimuli may cause separate activation of oxytocinergic neurons, terminating in the brain or the pituitary.

In this context oxytocin refers, whenever applicable, in addition to oxytocin also to precursors, metabolic derivatives, oxytocin agonists or analogues displaying the same properties.

Substances with oxytocin activity according to the invention can be described by the general formula (SEQ ID No: 10)

wherein

W is selected from the group consisting of Ile, Cha, Val, Hoph and Phe;

X is selected from the group consisting of Gln, Ser, Thr, Cit, Daba and Arg;

Y is selected from the group consisting of Leu, Ile, Arg, Hos, Daba, Cit and Val; where Leu, Ile and Val give oxytocin analogues and Arg, Hos, Daba and Cit give vasopressin analogues; and Z is selected from the group consisting of Gly and Ala.

The unnatural amino acids in said substances have the following structures:

Said amino acids are all commercially available, for instance from Bachem and Sigma.

The amino acids in the substances according to the invention can be either L- or D-amino acids.

Substances according to the invention also include nonapeptides having sequences with reversed peptide bonds. These sequences are preferably inverted sequences; more preferably comprising D-amino acids.

The nonapeptides of the formula I are believed to present oxytocin activity owing to the structural similarity to oxytocin having the formula (SEQ ID No: 11):

In the oxytocin structure the positions 1, 2, 5, 6 and 7 have remained unchanged, that is the disulfide bridge, and the amino acids believed to stabilize said bridge and to be of critical importance for the properties, that is Tyr in position 2, Asn in position 5 and Pro in position 7. In position 3 the hydrophobic Ile can be exchanged for other hydrophobic amino acids and in position 4 the hydrophilic Gln can be exchanged for other hydrophilic amino acids. In position 8 oxytocin analogues are obtained if Leu is exchanged for the hydrophobic amino acids Ile or Val, and vasopressin analogues are obtained if exchanged for the hydrophilic amino acids Arg, Hos, Cit or Daba. The nonapeptides of the invention have been compiled through methods described by S. Hellberg et al., "Peptide Quantitative Structure-Activity Relationships, a multivariate approach", J. Med. Chem. 1987, 30, 1126 and J. Jonsson et al., "Multivariate parametrization of 55 coded and non-coded amino acids" Quant. Struct.-Act. Relat., 8. 204–209 (1989). The peptides can be synthezised according to known methods (e.g. Merrifields solid phase synthesis for instance as described in Streitwieser and Heathcock, Introduction to Organic Chemistry 3rd ed, p 949–950.) Sequences with reversed peptide bonds can also be prepared through e.g retro-inverso-modification (see e.g. S. Müller et al, PNAS vol 94 November 1997, 12545–12550).

The use of oxytocin constitutes a preferred embodiment of the invention.

Another preferred embodiment of the invention is the use of the substances mesotocin, isotocin, vasopressin or vasotocin having the formulas (SEQ ID No: 10):

Cys-Tyr-Ile-Gln-Asn-Cys-Pro-Ile-Gly-$NH_2$ (mesotocin) (when in formula I W=Ile, X=Gln, Y=Ile and Z=Gly)

Cys-Tyr-Ile-Ser-Asn-Cys-Pro-Ile-Gly-$NH_2$ (isotocin) (when in formula I W=Ile, X=Ser, Y=Ile and Z=Gly)

Cys-Tyr-Phe-G ln-Asn-Cys-Pro-Arg-Gly-$NH_2$ (vasopressin) (when in formula I W=Phe, X=Gln, Y=Arg and Z=Gly)

Cys-Tyr-Ile-Gln-Asn-Cys-Pro-Arg-Gly-$NH_2$ (vasotocin) (when in formula I W=Ile, X=Gln, Y=Arg and Z=Gly)

Other preferred substances for use according to the invention are:

Cys-Tyr-Cha-Cit-Asn-Cys-Pro-Arg-Gly-$NH_2$ (SEQ ID NO: 1),

Cys-Tyr-Val-Thr-Asn-Cys-Pro-Leu-Gly-$NH_2$ (SEQ ID NO: 2),

Cys-Tyr-Hoph-Thr-Asn-Cys-Pro-Val-Gly-$NH_2$ (SEQ ID NO: 3),

Cys-Tyr-Phe-Cit-Asn-Cys-Pro-Leu-Gly-$NH_2$ (SEQ ID NO: 4),

Cys-Tyr-Cha-Arg-Asn-Cys-Pro-Hos-Ala-$NH_2$ (SEQ ID NO: 5),

Cys-Tyr-Val-Daba-Asn-Cys-Pro-Daba-Ala-$NH_2$ (SEQ ID NO: 6),

Cys-Tyr-Hoph-Daba-Asn-Cys-Pro-Cit-Ala-$NH_2$ (SEQ ID NO: 7) and

Cys-Tyr-Phe-Arg-Asn-Cys-Pro-Val-Ala-$NH_2$ (SEQ ID NO: 8).

Experiments have shown that oxytocin by way of a central action increases the activity of the central $\alpha_2$-receptors in rats. These receptors have an inhibitory action and counteracts the activating aspects of noradrenalin in the brain which are mainly mediated via $\alpha_1$-receptors, which activate cyclic AMP. When $\alpha_2$-receptor stimulation dominates over $\alpha_1$-receptor stimulation, activity is exchanged by relaxation and energy is shunted towards growing and healing, i.e. is not used for stress or muscular contraction and activity. As a consequence parasympathetic nerve tone dominates over sympathetic nervous tone and the musculature is relaxed. It can be presumed that oxytocin exerts a similar effect also in humans. During breast feeding—a situation characterized by repetitive oxytocin secretion—all the effects observed in experimental animals following repeated oxytocin administration are seen. It is not known how the effect by oxytocin on $\alpha_2$-receptors is mediated, but probably not by a classical oxytocin receptor mediated effect.

The effect of oxytocin can be extended or strengthened by administration in combination with drugs increasing the release of oxytocin and/or the number of receptors, such as estrogen, or drugs having an $\alpha_2$-agonistic effect, such as clonidine.

The invention also refers to the use of oxytocin in combination with estrogen for the preparation of a pharmaceutical composition for a curative or prophylactic wound healing. Oxytocin and estrogen are either administrated together or estrogen is given first and oxytocin subsequently. Estrogen increases release and synthesis of oxytocin, the synthesis of oxytocin receptors, and it also upregulates the activity of $\alpha_2$-receptors.

The short term effects of oxytocin, such as short term pain relief, short term sedation and hormone release, are reversed by oxytocin antagonists and can thus be described as direct effects.

The long term effects, amounting to days-months of relief, which are obtained after repeated treatments, for 3–10 days, preferably for 5–8 days, in intervals ranging from weeks to months, are surprising also in a general perspective and have not previously been reported for any other drug in patients. When said effect has been obtained it can be maintained by for instance once in a week treatment. This long term effect is reversed by $\alpha_2$-antagonists and potentiated by $\alpha_2$-agonists.

The pharmaceutical composition containing oxytocin can be formulated for topical, iontophoretical, nasal, intrapulmonary, parenteral, such as subcutaneous, intraperitoneal or intravenous, intrathecal or intracerebroventricular administration. The preferred ways of administration are topically and intranasally. A parenteral composition is for instance a solution or emulsion for subcutaneous, intra-muscular or intravenous injection. A topical composition can be a lotion, cream, ointment or gel, for instance incorporated into a plaster.

Doses to be given in topical administration can be 1–1000 $\mu g/cm^2$, preferably 10–100 $\mu g/cm^2$; in parenteral administration 0.05–1 mg/kg; and in nasal administration 1–100 IU/d, preferably 25–50 IU/d. 1 IU or international unit corresponds to 2 $\mu g$. To children with navel colic a preferred dose might be 20–50, preferably 25–30 IU/d nasally, preferably administered 2–3 times during 1–2 hours. In i.c.v. or i.t. administration the doses are generally 1/10 to 1/1000 of the parenteral doses.

In the market there are today commercial solutions for injection and nasal sprays.

BIOLOGICAL TESTS

An established model of wound healing is to investigate the survival of musculocutaneous flaps in rats. In plastic surgery, reconstructive problems are often solved by surgical flaps. The main disadvantage of surgical flaps has been their tendency to develop ischemia and eventually necrosis of the distal part. This complication can in the end ruin what postoperatively seemed to be an excellent result. Much research has been devoted to explain the mechanisms of surgical skin flap survival and how to prevent and reverse established ischemia.

For studying the effects of cutaneous wound-healing agents on chronic non-healing dermal ulcers the mutant C57BL/Ks-db/db diabetic mouse has emerged as a potentially relevant healing-impaired model. These homozygous genetically diabetic mice develop obesity and hyperglycemia that is resistant to insulin, analogous to human type II diabetes. They also show signs of diabetes such as excessive drinking and urination and greatly elevated urinary glucose levels. Wounds in these mice exhibit a marked delay in cellular infiltration, granulation tissue formation, and wound closure. Previous studies have used this model to evaluate formulations of aFGF.

Test 1. Survival of flaps in rats after administration of oxytocin

The aim of this study was to investigate the effects of oxytocin on the survival of musculocutaneous flaps in rats.

71 female albino rats (Sprague-Dawley, weight 180–220 g) were anaesthetized with chloralhydrate (0.4 g/kg), shaved on the back and a dorsal cranially based standard flap (2×7 cm) was elevated and then sutured back in position. The flap was raised from the deep fascia of muscle and included the superficial fascia, panniculus carnosus, subcutaneous tissue and skin. 24 h and 1 h before operation, respectively, as well as 24 h after operation the rats were treated with 1 mg/kg oxytocin s.c. (n=20), an oxytocin antagonist, that is 1-deamino-2-D-Tyr-(OEt)-4-Thr-8-Orn-oxytocin in an amount of 1 mg/kg (n=15), with 1 mg/kg of said oxytocin antagonist and then after 30 minutes with 1 mg/kg oxytocin (n=16), or with saline (n=20).

Six days after the operation the survival of the flaps were estimated. The oxytocin-treated rats had a significantly higher survival of the flaps when compared to the saline-treated controls (p<0.05). When the oxytocin antagonist was administrated before the oxytocin injection this effect was abolished. The oxytocin antagonist alone decreased the flap survival compared to the saline-treated rats (no significance, p=0.13) and the oxytocin-treated rats (p<0.05).

Figure 1:
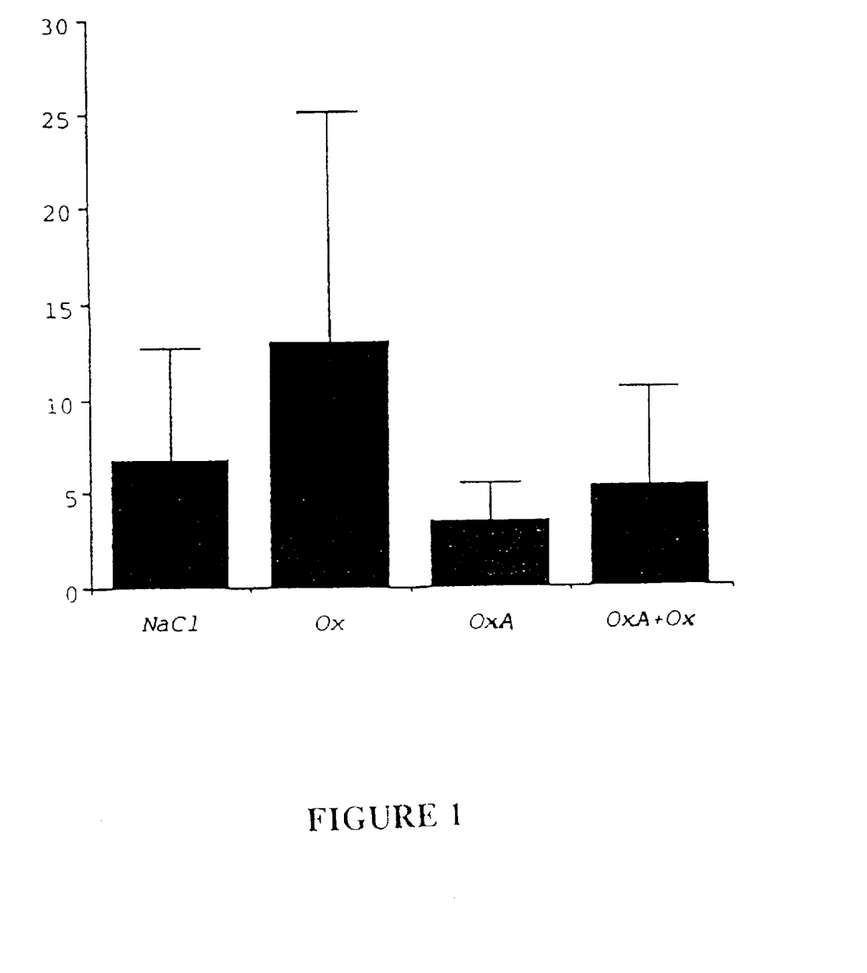
FIG. 1 is a bar graph of the survival of musculocutaneous flaps in rats after s.c. administration of oxytocin and oxytocin antagonist.

The result of the study is demonstrated in FIG. 1, showing the survival of musculocutaneous flaps in rats treated s.c. with saline (NaCl), oxytocin (Ox), oxytocin antagonist (OxA) and oxytocin antagonist+oxytocin (OxA+Ox). The results are shown as means±SD. Statistical evaluation was performed with a one-way ANOVA followed by Student's t-test.

Test 2. Wound healing in diabetic mice after administration of oxytocin

Female C57BL/Ks-db/db diabetic mice, 11 weeks old, were obtained from Jackson Laboratories (Bar Harbor, Me.). The mice were housed in sterile microisolator boxes (four per box) with sterile water and bedding and were kept in a semi-barrier quarantine facility. Supplemental heat was provided with electric heating pads under half of each box after wounding to prevent hypothermia and reduce mortality.

Mice were anesthetized with intraperitoneal injections of 110 mg ketamine and 9 mg xylazine per kg of body weight. The mid-back and thoracic skin was shaved and disinfected with a 2% Chlorhexidine surgical scrub, followed by 70% ethanol. A template 1.6 cm in diameter was used to mark a 2.0 $cm^2$ circle on the mid-dorsal area, and a single full-thickness wound was created by blunt excision with sterile curved iris scissors. Wound areas typically increased to approximately 2.3 cm² soon after injury, presumably because of contraction of the dermis along the wound perimeter. All surgical and subsequent healing analysis procedures were performed in a laminar flow hood using full aseptic techniques. Doses were administrated on 5 consecutive days before, and on day 0, 3 and 7 after injury. Oxytocin was administered at different doses, 0.001, 0.01, 0.1, 1.0, 10.0 and 100.0 μg/cm², respectively, to groups of 16 mice per dose. The wounds were covered with a semitransparent Bioclusive dressing (Johnson & Johnson Products, New Brunswick, N.J.) for protection, maintenance of a moist environment and prevention of crust formation. Wound fluid samples were taken at day 10 after injury and cultured for aerobic and anaerobic microorganisms. Animals from which cultures exhibited more than 50 colonies per wound were excluded from the study analysis. Prevention of even mild or subclinical infection resulted in a consistent maximal healing impairment, thus providing a large wound-healing window for evaluation of treatment effects.

Wound appearances were recorded photographically and their perimeters were traced onto sterile glass slides applied directly to the exposed wound surfaces after pre-wetting with a drop of sterile physiologic saline. Measurements were made immediately after wounding and twice weekly thereafter until the wounds were completely closed. Wound areas and perimeters were determined from the glass-slide tracings using computerized image analysis. Statistical significances of differences between groups were evaluated using an unpaired two-tailed Student t-test.

Healing expressed as a decrease in percent initial area was converted to linear ingrowth from the wound edges by dividing the differences in wound areas by the average wound perimeters at sequential time intervals. Total ingrowth at a specific time is the sum of the incremental ingrowth distances up until that time. This transformation linearized closure as a function of time, thereby allowing expression of healing as kinetic rates that were constant over time.

Wounds, examined twice weekly to monitor time to total closure, were considered fully healed when moist granulation tissue was no longer apparent, indicating a functional epidermal water-permeability barrier. Closure was also confirmed histologically. Time-point comparisons of the fraction of healed versus unhealed wounds were analyzed by the $X^2$ statistic with Yates correction, and group comparisons of absolute days to total closure for individual animals were analyzed by an unpaired two-tailed Student t-test.

Full-thickness dermal excisional wounds 1.6 cm in diameter closed substantially faster in response to three doses of 10 μg per cm² initial wound area administered during the first week after wounding compared with treatment with the corresponding vehicle control. Statistically significant enhancements of the healing rate ($p \leq 0.01$) of treated wounds were seen as early as day 7 after injury and continued throughout the test period. A 50% maximum difference in percent of initial area between oxytocin and vehicle-treated wounds occurred from 14 d after injury. This difference corresponded to a 10-fold decrease in wound size in treated mice at day 14 compared with those receiving the corresponding PBS/heparin vehicle. Although wounds receiving a liquid vehicle healed somewhat faster than wounds receiving nothing, treatment with either PBS or normal saline resulted in healing rates equivalent to those with the heparin-containing PBS vehicle (data not shown).

Wound closure was nonlinear as a function of time, so the magnitude of the effect of oxytocin treatment appeared to change over time. Because these full-thickness wounds closed by progressive healing from the wound perimeter, we transformed the data from percent initial wound area to average linear healing length from the original wound edges. This calculation linearized the average healing rates after an initial 3 d lag. Treatment with oxytocin significantly ($p \leq 0.01$) increased the linear rate of healing from the wound edges at all time intervals. The slope of cumulative linear healing length as a function of time was determined for each animal. These slopes, grouped by treatment, showed that 10 μg/cm² oxytocin increased the mean linear healing rate to 0.45 mm/d, from 0.18 mm/d observed in the vehicle-treated group ($p \leq 0.01$).

Treatment with this dose of oxytocin also clearly reduced the time to total wound closure. Statistically significant ($p \leq 0.05$) increases in total closure were seen by day 14. The median time to complete closure decreased from 52 d in vehicle-treated wounds to only 23 d in those treated with three doses of oxytocin during the first week after injury ($p \leq 0.0001$).

Three topical applications of oxygen, ranging from 1 to 100 μg/cm² per dose, applied during the first week after injury resulted in significant dose-related increases in healing rates over paired vehicle controls. The 0.001 μg/cm², 0.01 μg/cm² and 0.1 μg/cm² doses were ineffective, thus establishing a "no effect" level between 0.001 and 1 μg/cm².

A dose response relation was also seen in the time to complete wound closure. Application of from 1 to 100 μg/cm² per dose significantly reduced the time required for these wounds to close completely. In the dose range of 1.0 to 10.0 μg/cm², wounds closed approximately 10 d sooner than their respective vehicle controls. The closure rates, the 0.001–μg/cm² (not shown) and 0.01 μg/cm² doses were ineffective in decreasing the time to total closure.

The concentration of FGF was compared in skin biopsies taken from the injured area ("ulcer") of ten mice treated with 10 μg/cm² oxytocin and ten mice treated with PBS 7 days after injury. The results show that the oxytocin treated mice synthesized 162% more FGF-1 as compared to the PBS vehicle treated mice. This increase in concentration was highly significant ($p < 0.001$) and strongly support the hypothesis that oxytocin increases wound healing through an increased expression and synthesis of FGF-1.

What is claimed is:

1. A method for the curative treatment of wounds of the skin, bone, mucus, tendons, muscles or connective tissue in mammals comprising administering a substance with oxytocin activity in a pharmaceutical composition to a mammal in need of said treatment, said substance not being vasopressin.

2. A method according to claims 1, wherein said substance has the following formula I:

$$\text{Cys-Tyr-W-X-Asn-Cys-Pro-Y-Z-NH}_2 \quad\quad (\text{I})$$
with a disulfide bond S—S between the two Cys residues.

wherein

W is selected from the group consisting of Ile, Cha, Val, Hoph and Phe; X is selected from the group consisting of Gln, Ser, Thr, Cit, Daba and Arg; Y is selected from the group consisting of Leu, Ile, Arg, Hos, Daba, Cit and Val; and Z is selected from the group consisting of Gly and Ala; as well as sequences with reversed peptide bonds; with the exception of vasopressin.

3. A method of claim 1, wherein said substance is oxytocin.

4. A method of claim 1, wherein said substance is mesotocin, isotocin or vasotocin.

5. A method of claim 1, wherein said substance is oxytocin in combination with estrogen.

6. A method of claim 1, wherein said substance is in the form of a pharmaceutical composition comprising oxytocin in combination with a pharmaceutically inert carrier.

7. A method according to claim 1, wherein said administering comprises nasal administration of 5–100 IU oxytocin per day.

8. A method according to claim 1, wherein said administering comprises administration of 25–50 IU oxytocin per day.

9. A method of claims 1, wherein said substance is selected from the group consisting of:

10. A method of claim 1, wherein said wounds are chronic wounds.

11. A method of claim 1, wherein said substance is in the form of a pharmaceutical composition formulated for nasal or topical administration.

12. A method according to claim 1, wherein said administering comprises nasal or topical administration.

13. A method according to claim 1, wherein said substance is in the form of a pharmaceutical composition in the form of a nasal spray.

14. A method for the curative or prophylactic treatment of wounds of the skin, bone, mucus, tendons, muscles, nerves, vessels or connective tissue in mammals comprising administering a substance with oxytocin activity in a pharmaceutical composition to a mammal in need of said treatment, wherein said substance is selected from the group consisting of:

and

15. A method of claim 14, wherein said wounds are chronic wounds.

16. A method of claim 14, wherein said substance is in the form of a pharmaceutical composition formulated for nasal or topical administration.

17. A method according to claim 14, wherein said administering comprises nasal or topical administration.

18. A method according to claim 14, wherein said substance is in the form of a pharmaceutical composition in the form of a nasal spray.

19. A method for the curative or prophylactic treatment of wounds in mammals by activating at least one of growth factors and growth factor receptors comprising administering a substance with oxytocin activity in a pharmaceutical composition to a mammal in need of said treatment, wherein said substance is selected from the group consisting of:

-continued

Cys-Tyr-Hoph-Daba-Asn-Cys-Pro-Cit-Ala-NH$_2$ (SEQ ID NO: 7)

and

Cys-Tyr-Phe-Arg-Asn-Cys-Pro-Val-Ala-NH$_2$. (SEQ ID NO: 8)

20. A method of claim 19, wherein said substance is in the form of a pharmaceutical composition formulated for nasal or topical administration.

21. A method according to claim 19, wherein said administering comprises nasal or topical administration.

22. A method according to claim 19, wherein said substance is in the form of a pharmaceutical composition in the form of a nasal spray.

* * * * *

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<221> NAME/KEY: MOD_RES
```

```
<222> LOCATION: (9)
<223> OTHER INFORMATION: AMIDATION
<221> NAME/KEY: DISULFID
<222> LOCATION: (1)..(6)
<223> OTHER INFORMATION: Xaa(3)=Cha
<223> OTHER INFORMATION: Xaa(4)=Cit
<223> OTHER INFORMATION: Description of Artificial Sequence:PEPTIDE

<400> SEQUENCE: 1

Cys Tyr Xaa Xaa Asn Cys Pro Arg Gly
 1               5

<210> SEQ ID NO 2
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
<222> LOCATION: (1)..(6)
<223> OTHER INFORMATION: Description of Artificial Sequence:PEPTIDE

<400> SEQUENCE: 2

Cys Tyr Val Thr Asn Cys Pro Leu Gly
 1               5

<210> SEQ ID NO 3
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
<222> LOCATION: (1)..(6)
<223> OTHER INFORMATION: Xaa(3)=Hoph
<223> OTHER INFORMATION: Description of Artificial Sequence:PEPTIDE

<400> SEQUENCE: 3

Cys Tyr Xaa Thr Asn Cys Pro Val Gly
 1               5

<210> SEQ ID NO 4
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
<222> LOCATION: (1)..(6)
<223> OTHER INFORMATION: Xaa(4)=Cit
<223> OTHER INFORMATION: Description of Artificial Sequence:PEPTIDE

<400> SEQUENCE: 4

Cys Tyr Phe Xaa Asn Cys Pro Leu Gly
 1               5

<210> SEQ ID NO 5
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
```

```
<222> LOCATION: (1)..(6)
<223> OTHER INFORMATION: Xaa(3)=Cha
<223> OTHER INFORMATION: Xaa(8)=Hos
<223> OTHER INFORMATION: Description of Artificial Sequence:PEPTIDE

<400> SEQUENCE: 5

Cys Tyr Xaa Arg Asn Cys Pro Xaa Ala
  1               5

<210> SEQ ID NO 6
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
<222> LOCATION: (1)..(6)
<223> OTHER INFORMATION: Xaa(4)=Daba
<223> OTHER INFORMATION: Xaa(8)=Daba
<223> OTHER INFORMATION: Description of Artificial Sequence:PEPTIDE

<400> SEQUENCE: 6

Cys Tyr Val Xaa Asn Cys Pro Xaa Ala
  1               5

<210> SEQ ID NO 7
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
<222> LOCATION: (1)..(6)
<223> OTHER INFORMATION: Xaa(3)=Hoph
<223> OTHER INFORMATION: Xaa(4)=Daba
<223> OTHER INFORMATION: Xaa(8)=Cit
<223> OTHER INFORMATION: Description of Artificial Sequence:PEPTIDE

<400> SEQUENCE: 7

Cys Tyr Xaa Xaa Asn Cys Pro Xaa Ala
  1               5

<210> SEQ ID NO 8
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<221> NAME/KEY: DISULFID
<222> LOCATION: (1)..(6)
<223> OTHER INFORMATION: Description of Artificial Sequence:PEPTIDE

<400> SEQUENCE: 8

Cys Tyr Phe Arg Asn Cys Pro Val Ala
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:PEPTIDE
<221> NAME/KEY: MOD_RES
<222> LOCATION: (9)
<223> OTHER INFORMATION: AMIDATION
```

```
<221> NAME/KEY: DISULFID
<222> LOCATION: (1)..(6)

<400> SEQUENCE: 9

Cys Tyr Ile Gln Asn Cys Pro Leu Gly
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:PEPTIDE
<221> NAME/KEY: MOD_RES
<222> LOCATION: (9)
<223> OTHER INFORMATION: AMIDATION
<221> NAME/KEY: DISULFID
<222> LOCATION: (1)..(6)
<221> NAME/KEY: MOD_RES
<222> LOCATION: (3)
<223> OTHER INFORMATION: I, Cha, V, Hoph or F
<221> NAME/KEY: MOD_RES
<222> LOCATION: (4)
<223> OTHER INFORMATION: Q, S, T, Cit, Daba or R
<221> NAME/KEY: MOD_RES
<222> LOCATION: (8)
<223> OTHER INFORMATION: L, I, R, Hos, Daba, Cit or V
<221> NAME/KEY: MOD_RES
<222> LOCATION: (9)
<223> OTHER INFORMATION: G or A

<400> SEQUENCE: 10

Cys Tyr Xaa Xaa Asn Cys Pro Xaa Xaa
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:PEPTIDE
<221> NAME/KEY: MOD_RES
<222> LOCATION: (9)
<223> OTHER INFORMATION: AMIDATION
<221> NAME/KEY: DISULFID
<222> LOCATION: (1)..(6)

<400> SEQUENCE: 11

Cys Tyr Ile Gln Asn Cys Pro Leu Gly
 1               5
```